United States Patent [19]

Barberet et al.

[11] Patent Number: Plant 5,808

[45] Date of Patent: Nov. 25, 1986

[54] CARNATION NAMED LONCARTO

[75] Inventors: Nicole Barberet; Yves Ducloux, both of Antibes, France

[73] Assignee: Laboratoire de Physiologie Vegetale de la Londe, Les Maures, France

[21] Appl. No.: 669,480

[22] Filed: Nov. 8, 1984

[51] Int. Cl.[4] ..... A01H 5/00

[52] U.S. Cl. ..... Plt/70

[58] Field of Search ..... Plt./70

*Primary Examiner*—Robert E. Bagwill

*Attorney, Agent, or Firm*—Charles W. Rummler; John B. Lungmus

[57] ABSTRACT

A new and distinct spray carnation characterized by its profuse production of small flowers having white petals fringed with cardinal red serrated margins, borne in relatively large numbers on each flowering stem which is of medium length, erect and rigid, the plant having a vigorous, upright and rather rigid growth habit with moderately abundant foliage.

1 Drawing Figure

BACKGROUND OF THE NEW PLANT

Our new spray carnation variety is the result of our breeding efforts carried on at La Londe-Lex-Maures-Var, France, since 1980 with the object of producing a new spray carnation having flowers of good quality, nice color and resistance to *Fusarium oxysporum,* borne on a plant having a vigorous and upright growth habit and good flower production.

Our new plant originated as a seedling produced by crossing selected individually identified carnations growing among our collection of distinctive plants maintained at La Londe for breeding purposes, this particular seedling being selected by us for propagation and test because of its distinctive and novel generally white flowers having a cardinal red margin extending around the apex end of each petal. This seedling appeared to have a profuse production of flowers and a good growth habit and because of these advantageous characteristics, this new plant was asexually reproduced under our direction at La Londe by means of cuttings; and propagation through several successive generations, by both cuttings and in vitro propagation, has demonstrated that the novel characteristics of this plant hold true from generation to generation and appear to be firmly fixed.

DESCRIPTION OF THE DRAWING

This new carnation cultivar is illustrated by the accompanying photographic drawing which shows, in full color, a typical arrangement of buds and flowers in various stages of opening borne on a single flowering stem, the colors shown being as nearly true to those specified herein as is reasonably possible to obtain by conventional photographic procedures.

DESCRIPTION OF THE NEW PLANT

The following is a detailed description of our new spray carnation cultivar based upon observations of greenhouse grown plants made at La Londe, France in the spring of 1984. The color designations are specified according to The R.H.S. Colour Chart published by The Royal Horticultural Society of London, England.

THE PLANT

Origin: Seedling.

Parentage:

*Seed parent.*—Stock Plant No. 8563 V.

*Pollen parent.*—Stock Plant No. CEA 26. These parent plants are unpatented and unnamed varieties which are individually identified in our permanent records and are maintained in our collection of carnation plants at Laboratoire de Physiologie Vegetale de la Londe to provide stock for breeding purposes.

Classification:

*Botanic.—Dianthus caryophyllus.*

*Commercial.*—Spray carnation.

Form: An erect bush with at least four stems being emitted near the ground.

Plant Height: About 100 cm. in average.

Branching Character: The branching habit of this plant is normal.

Growth Habit: Vigorous and upright with rather rigid stems.

Foliage:

*Quantity.*—Moderately abundant.

*Number of leaves.*—At least 120.

*Size of Leaf.*—About 10.6 cm. long and about 0.7 cm. wide, in average, at the seventh node.

*Shape of leaf.*—Linear with straight margins and acuminate apex.

*Texture.*—Leathery.

*Color.*—Upper and under sides, Green 189A.

*Ribs and veins.*—Hardly noticeable.

*Rachis.*—Hardly noticeable.

THE BUD

Form: Long cylindrical.

Size:

*Diameter.*—About 1.1 cm. in average.

*Length.*—About 2.8 cm. in average.

Rate of opening: Normal.

Color of petals: When petals first divide and as the petals begin to unfurl, white with cardinal red margins.

Sepals: Number—5 to 6. The sepals are joined at the lower part and are of a generally oblong shape with a mucronate apex. The petals are hooded over the bud and as the flower opens the sepals continue to stand up.

Color:

*Inside.*—Green 138D.

*Outside.*—Green 138A in the main body portion and 143C in the apex portion.

Striae: Longitudinal.

Calyx:

*Shape.*—Long cylindrical.

*Aspect.*—Smooth.

*Splitting.*—The calyx does not split.

Flowering stem:

*Length.*—About 69 cm.

*Character.*—Erect and rather thin.

*Color.*—Grayed Green 189A.

THE FLOWER

Blooming habit: Recurrent, blooming profusely during the midseason of spring and fall with a tendency to give few blooms in fall.

Size of bloom: Small.

*Diameter.*—About 4.8 cm. in average.

*Depth.*—About 4.3 cm. in average.

Borne: On single stems of various lengths branching in simple raceme manner from the flowering stem.

Shape:

*When bloom first opens.*—High centered.

*As bloom matures.*—Rather flat.

Petalage:

*Number of petals.*—23 in average.

*Arrangement.*—Imbricated.

*Form.*—Fan-shaped with slightly undulated and serrated margins.

*Texture.*—Leathery.

*Appearance.*—Shiny.

*Color.*—Outer and inside petals: Body — White 155D with Cardinal Red 53A margin. Base — Pale greenish-yellow. Reverse side — White 155D and Greyed Purple 185B.

Petaloids: Rarely occurring.

*Size.*—Smaller than petals.

*Color.*—Same as petals.

Flowering stem:

*Length.*—About 69 cm. in average.

*Character.*—Upright and of good strength.

*Color.*—Greyed Green — 189A/B.

Fragrance: Absent or very light.

Persistence: The flowers hang on and dry.

Lasting quality: As a cut flower—At least ten days in vase keeping.

Disease resistance: Resistant to *Fusarium oxysporum* as observed INRA-Antibes-06-France.

REPRODUCTIVE ORGANS

Stamens:

*Number.*—9 to 16.

*Arrangement.*—Encircling the ovary.

*Anthers.*—Size: Less than 4 mm. Color: Whitish.

*Filaments.*—Length: About 3 cm. Color: Whitish.

Pistils:

*Number.*—Two.

*Styles.*—Length: About 2 cm. in average. Color: Whitish.

*Stigma.*—Color: Lightly purplish blue.

Character of ovaries: Smooth.

The expression of the above characteristics can be more-or-less strongly modulated under the influence of the environment conditions, i.e., ground, method of cultivation, latitude, etc. These data are based upon observations made in the spring of 1984 in the southern part of France.

We claim:

1. A new and distinct spray carnation cultivar, substantially as herein shown and described, characterized by the white petals of its small flowers which have serrated margins of cardinal red color, the flowers being profusely produced during each of the recurrent blooming seasons and the plant having a vigorous growth habit and being resistant to *Fusarium oxysporum.*

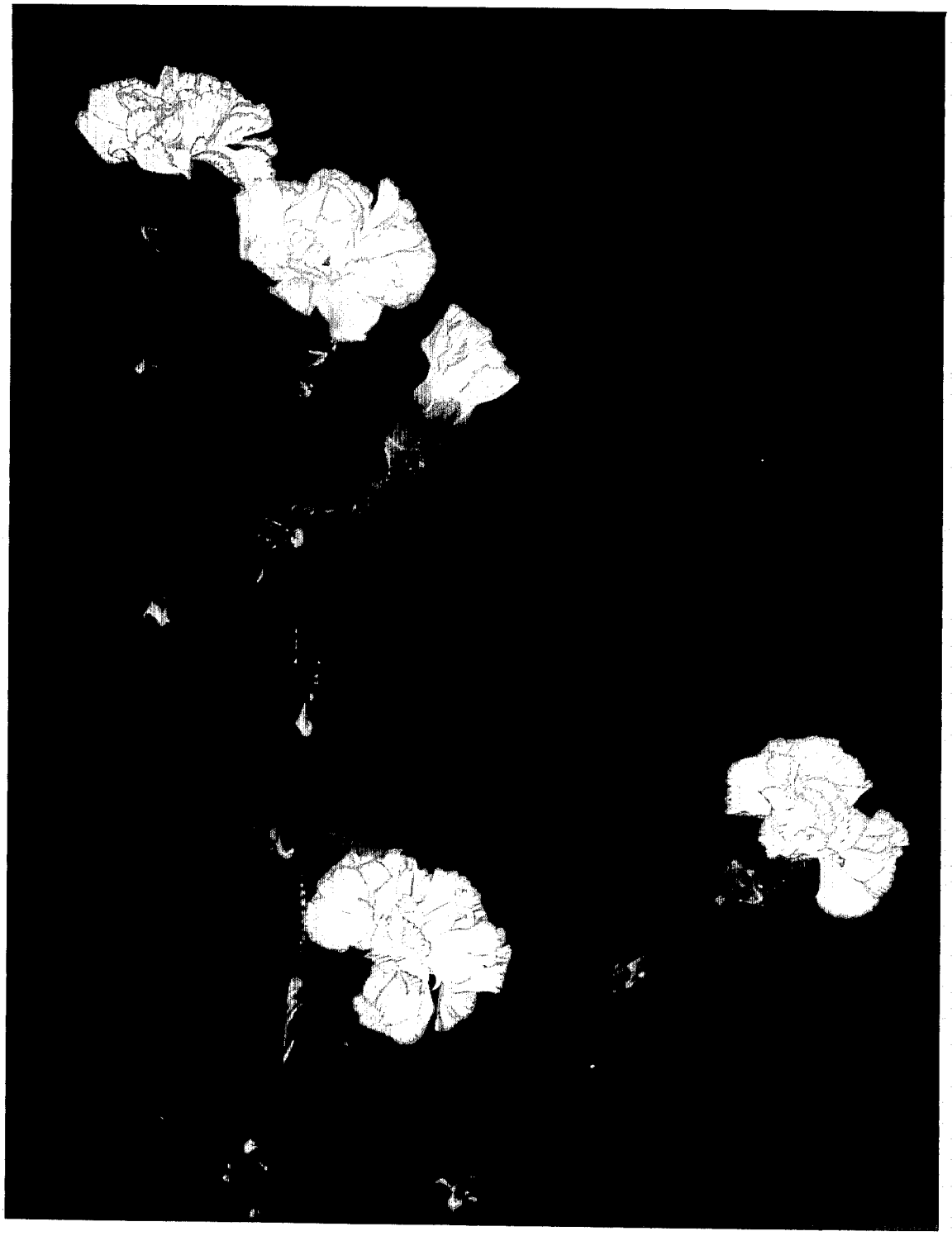

* * * * *